US011679175B2

(12) United States Patent
Rigby

(10) Patent No.: US 11,679,175 B2
(45) Date of Patent: Jun. 20, 2023

(54) APPARATUS AND METHODS FOR DIFFUSING ESSENTIAL OIL

(71) Applicant: Warner William Rigby, St. George, UT (US)

(72) Inventor: Warner William Rigby, St. George, UT (US)

( * ) Notice: Subject to any disclaimer, the term of this patent is extended or adjusted under 35 U.S.C. 154(b) by 533 days.

(21) Appl. No.: 16/745,191

(22) Filed: Jan. 16, 2020

(65) Prior Publication Data

US 2020/0222575 A1 Jul. 16, 2020

Related U.S. Application Data

(60) Provisional application No. 62/940,765, filed on Nov. 26, 2019, provisional application No. 62/792,973, filed on Jan. 16, 2019.

(51) Int. Cl.
*A61L 9/16* (2006.01)
*A61L 9/03* (2006.01)
*F24F 6/12* (2006.01)

(52) U.S. Cl.
CPC .................. *A61L 9/16* (2013.01); *A61L 9/03* (2013.01); *F24F 6/12* (2013.01); *A61L 2209/13* (2013.01); *F24F 2203/02* (2013.01); *F24F 2221/12* (2013.01)

(58) Field of Classification Search
CPC .......... A61L 9/16; A61L 9/03; A61L 2209/13; A61L 2209/132; A61L 2209/135; A61L 9/122; A61L 9/032; F24F 6/12; F24F 2203/02; F24F 2221/12
See application file for complete search history.

(56) References Cited

U.S. PATENT DOCUMENTS

| | | | |
|---|---|---|---|
| 2003/0097936 A1* | 5/2003 | Maleeny | A61L 9/12 96/222 |
| 2005/0031511 A1* | 2/2005 | Nohara | A61L 9/015 422/123 |
| 2013/0320574 A1* | 12/2013 | Sickinger | A61L 9/122 261/30 |
| 2018/0135875 A1* | 5/2018 | Seo | F24F 13/08 |

OTHER PUBLICATIONS

Fairlliscrafts, Etsy, Listing Date at the Bottom of the Page (Year: 2018).*

* cited by examiner

*Primary Examiner* — Sean E Conley
*Assistant Examiner* — Brendan A Hensel
(74) *Attorney, Agent, or Firm* — Dax D. Anderson; Kirton McConkie

(57) ABSTRACT

A essential oil diffuser that gasifies a liquid, such as water, which passes through a screen where it picks up essential oil and diffuses it into the ambient air.

19 Claims, 2 Drawing Sheets

APPARATUS AND METHODS FOR DIFFUSING ESSENTIAL OIL

CROSS-REFERENCE TO RELATED APPLICATIONS

This application claims priority to Provisional Patent Application Nos. 62/792,973, filed 16 Jan. 2019, entitled "Steamy Mug," and 62/940,765, filed Nov. 26, 2019, entitled "Essential Oil Diffuser," which are incorporated herein in their entirety.

TECHNICAL FIELD

The present disclosure relates generally to diffusing essential oils into the ambient air. More particularly, the disclosure relates to a receptacle configured to vaporize a liquid, generally water or a similarly suitable liquid, channeling the vapor through a foil to improve the interaction between the vapor and a substrate comprising an essential oil and diffusing the liquid into the air.

BACKGROUND

Aromatherapy improves psychological and physical well-being through the use of plant materials and aromatic plant oils, including essential oils. Diffusers provide a well-known mechanism for delivering the essential oils into the ambient air. Despite thus use of diffusers, a need exists to improve the delivery of highly concentrated essential oils in a diffuser. Thus an apparatus is needed to improve the delivery of diffused essential oils.

BRIEF SUMMARY

The general purpose of the systems and methods disclosed herein is to provide an improved diffuser that allows for the improved delivery of concentrated essential oils. Specifically, an apparatus that generates a vapor and directs it toward a substrate comprising an essential oil so as the vapor and the substrate interact for a longer time, thus improving the diffusion of the essential oil into the ambient air.

In one non-limiting embodiment, a vaporizer, that can deliver hot or cold vapor, generates a vapor which passes through a lid comprising a plurality of vents. The lid is further formed into a foil which directs the flow of vapor to a substrate comprising an essential oil.

BRIEF DESCRIPTION OF THE DRAWINGS

In order to describe the manner in which the advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

Figure 2A:
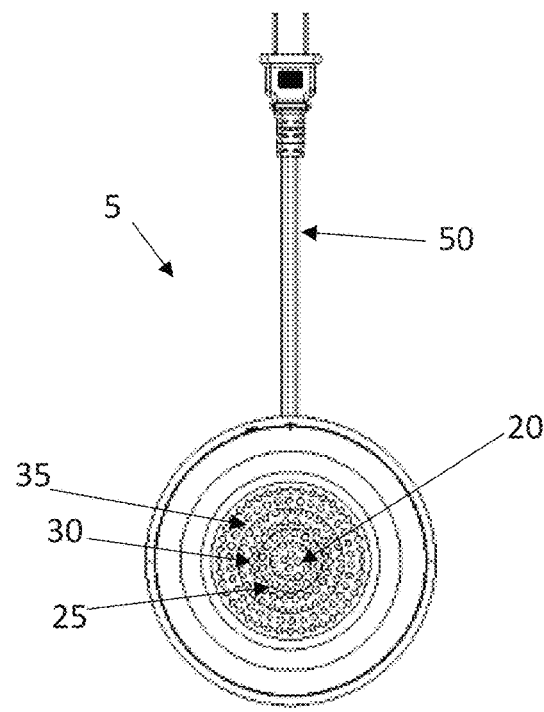
FIG. 2A shows a top view of the vaporizer with the lid.
Figure 2B:
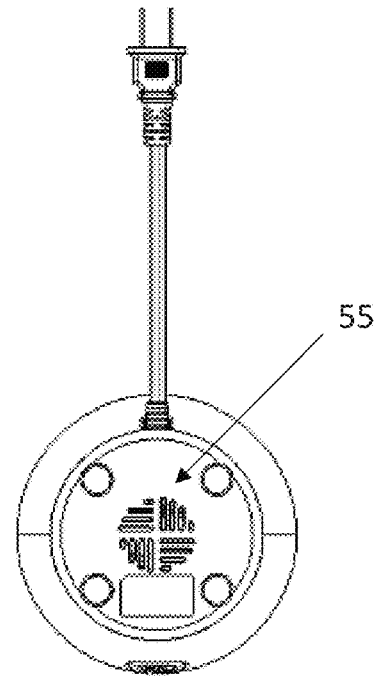
FIG. 2B shows a bottom view of the vaporizer.
Figure 3A:
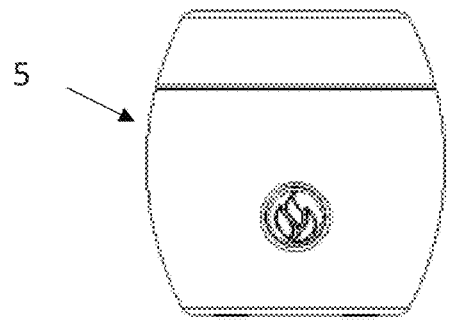
FIG. 3A shows a side view of the vaporizer.
Figure 3B:
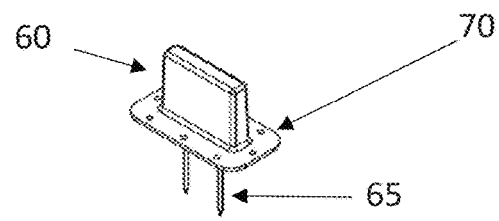
FIG. 3B shows a detailed view of the vaporizing element.

The present embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed descriptions of the embodiments of the apparatus, as represented in FIGS. 1 through 3 are not intended to limit the scope of the invention, as claimed, but are merely representative of present embodiments of the invention.

In general, the figures disclose an invention that provides an essential oil diffuser with an foiled lid configured to improve the flow of vapor around a substrate to diffuse the essential oil into the ambient air.

In the following description, numerous references will be made to essential oils and substrates, but these items are not shown in detail in the figures. However, it should be understood that one of ordinary skill in the art and in possession of this disclosure, would readily understand how the present invention and essential oils and substrates can be incorporated.

Figure 1:
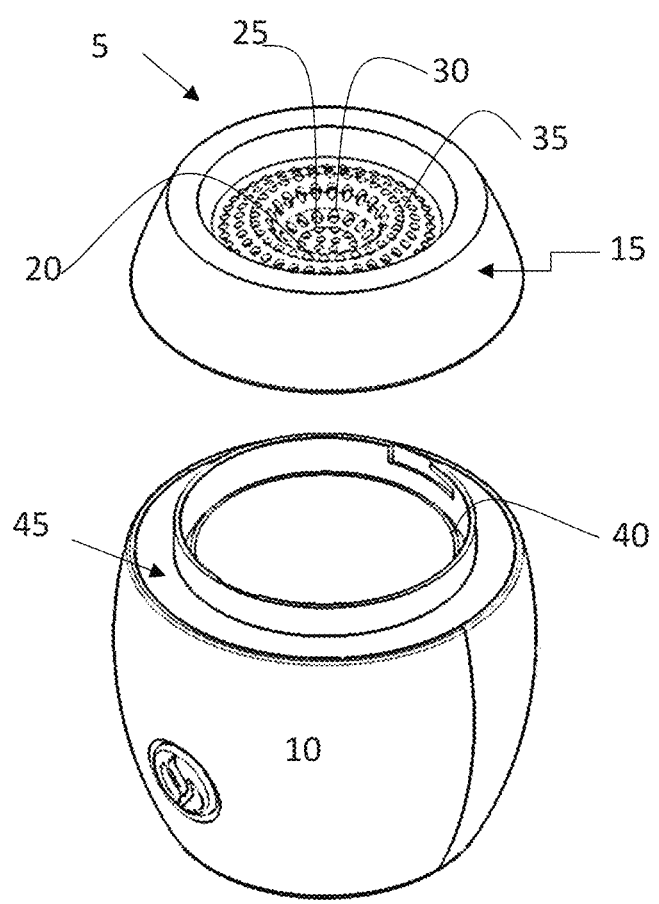
FIG. 1 shows a detailed perspective view of the vaporizer.

Detailed references will now be made to the preferred embodiments of the present invention, examples of which are illustrated in FIG. 1 illustrates a view of diffuser 5 in accordance with one or more embodiments of the invention. In some embodiments the diffuser comprises a vapor generator wherein a receptacle housed inside the container is configured to gasify a fluid. In some embodiments the vapor generator generates water steam. In some embodiments the vapor generator generates vapor from oils, lotions, certain vinegars and alcohol including isopropyl alcohol. In some embodiments the diffuser comprises a container 10 with a hollow center configured to receive a liquid. In some embodiments the container body 10 is made of plastic, or wood, or any other material with a sufficiently high melting point. In some embodiments the container comprises an insulating layer to shield the exterior of the container from temperature variations inside the container 10. In some embodiments the container 10 comprises an opening on the top of the container 10 configured to receive the liquid and through which the liquid vapor can escape.

In some embodiments the diffuser 5 comprises a lid 15 which is configured to cover the container 10 opening. In some embodiments the lid 15 comprises an annular ring with a hollow center. In some embodiments the lid 15 is configured to selectively secure to the container 10. In some embodiments the lid 15 rests on the lip 45 of the container.

In some embodiments the lid 15 comprises a vented screen 20 which is nested in the annular ring. In some embodiments the vents are distributed across the surface of the screen 20. In some embodiments the screen 20 is configured to direct gasses escaping from the container 10 toward a location on the screen.

In some embodiments the screen 20 comprises a series of air foils 25, 30 and 35. In some embodiments the air foils are configured to direct and recirculate gasses escaping from the container 10. In some embodiments the foils are designed to concentrate the gasses towards the center of the screen where the gasses will circulate at the center of the screen before being diffused into the ambient air. In some embodiments the screen 20 is bent in a first in a first direction, such as away from the container 10. In some embodiments the screen 20 is bent in a second direction, such as folded over itself and back towards the container 10. In some embodiments the screen 20 is bent back in the first direction, thus creating a depression in the center of the screen 20, and then rising from the center as the screen radiates from the center to the edge. In some embodiments the screen 20 reaches a nadir and drops back down where it connects to the annular ring in the lid 15. In some embodiments the screen 20 is configured to allow vapor pressure to build up under the ridge to improve the pressure of the gas escaping from the container 10 as it enters the screen depression 20. In some embodiments the vents in the screen 20 are selectively closable to allow increased ability to direct gasses escaping from the container 10.

In some embodiments a substrate (not shown) is placed in the depression. In some embodiments the substrate comprises an essential oil contained in a matrix. In some embodiments the substrate comprises a porous rock, such as lava rock. In some embodiments the substrate comprises a wax. In some embodiments the substrate comprises a super absorbing polymer. In some embodiments the substrate comprises wood or other fibrous material that can absorb an essential oil. In some embodiments the substrate is a sponge or other cellulose material which absorbs the essential oil. In some embodiments the substrate is configured to nest within the depression in the screen 20 so as to interact with the maximum amount of vapor escaping from the container 10 under the highest available pressure for the longest period of time. In some embodiments the substrate may be placed on the outside of the screen 20 proximal the annular wall of the lid 15. In some embodiments different substrates of essential oils may be combined by placing a first substrate in the center of the screen 20 and a second on the outside of the screen.

In some embodiments the container comprises a gasifying element 60 configured to gasify the liquid in the container 10. In some embodiments the gasifying element 60 is a heating element configured to heat the liquid and increase its vapor pressure. In some embodiments the gasifying element is sonicator that uses ultrasonic waves to atmoize the liquid for dispersion as a vapor. When the embodiment comprises liquid water the heat element creates steam which escapes through the screen 20, passes over the substrate, combines with essential oil vapor and then diffuses the essential oil into the ambient air. In some embodiments the heat of the steam provides further activation energy to the essential oils to vaporize and combine with the steam. In some embodiments the cold vaporization such as the ultrasonic atomization allows the microdroplets to condense on the substrate and mix with the essential oil before combining with water vapor and diffusing into the ambient air.

In some embodiment the gasifying element 60 which is a heater is placed in the center of the fluid reservoir to allow the fluid to be heated from the middle, thus accelerating the vaporization of the liquid. In some embodiments the gasifying element 60 is a heat plate positioned outside a selectively removable receptacle 40 wherein the receptacle 40 is heated, thus heating the liquid.

In some embodiments the invention comprises a method of diffusing an essential oil comprising placing a liquid in a receptacle 40. In some embodiments the method further comprises vaporizing the liquid. In some embodiments the invention comprises passing the water through a vented lid wherein the lid comprising foils and vents that direct the vapor to engage a substrate comprising an essential oil. In some embodiments the method further comprises diffusing the essential oil into the ambient air. In some embodiments the method further comprises providing a screen 20 with a plurality of foils 25, 30, 35 wherein the foils are configured to direct the vapor passing through the screen to a desired location above the screen, such as to the center. In some embodiments the method further comprises bending the screen 20 to form a first foil. In some embodiments the method further comprises bending the screen 20 in a second direction. In some embodiments the method further comprises heating the fluid. In some embodiments the method further comprises atomizing the fluid into a vapor using ultrasonic waves.

In some embodiments a container 10 comprises a small cylindrical unit that produces a constant source of steam using rechargeable battery power. In some embodiments the battery powers a small heating unit that heats a small water reservoir to produce the steam. In some embodiments the reservoir is located within the unit and the steam passes through a protective vent that prohibits the water from freely spilling from the reservoir. The top may be removed allowing access to the water reservoir. In some embodiments the container 10 comprises PP medical grade non-corrosive plastic, so it is compatible with essential oils. In some embodiments the present invention is intended to be used as a tool for aromatherapy for essential oils by pressing the power button, the unit heats to a set temperature and produces continuous steam until the water reservoir is depleted or the unit is turned off. In some embodiments the present invention is also waterproof.

In some embodiments the vapor generating apparatus comprises a receptacle with an inner chamber configured to receive water. In some embodiments the receptacle is made of metal, or a composite, or earthen materials. In some embodiments the vapor-generating apparatus comprises a heat element which heats the contents of the receptacle. In some embodiments the apparatus vaporizes the contents of the receptacle by an ultrasonic vibrator or a spinning disc which particleize or atomizes the water into droplets. In some embodiments the apparatus comprises a fan which pulls the vapor from the receptacle and disperse it into the adjacent atmosphere. In some embodiments a current is created by the temperature of the vapor, such as when steam is created, and the hot steam naturally rises above the cooler unheated air.

In some embodiments the apparatus comprises a screen. In some embodiments the screen allows the vapor to escape from the inner chamber. In some embodiments the screen forms the top surface of the apparatus. In some embodiments the screen comprises a portion of the top surface of the apparatus. In some embodiments the scree comprises a side portion of the apparatus. In some embodiments the screen comprises a cup, cavity or depression. In some embodiments the depression comprises an air foil to direct the air flow passing over the cup. In some embodiments the cup is made of the screen material. In some embodiments the screen is solid while the area around the cup is the screen material. In some embodiments the cup is a different screen pattern than the material. In some embodiments cup comprises vents placed to modulate the air flow through the cup. In some embodiments the air flow through the vents can be selectively modulated to selectively increase or reduce the air flow through the cup.

In some embodiments a oil-bearing material is a substrate placed in the vapor flow. In some embodiments the oil-bearing material is a salt crystal such as Himalayan salt. In some embodiments the oil-bearing material is a porous stone such as pumice or volcanic stone. In some embodiments the material is a sponge.

According to some embodiments the oil-bearing material absorbs or adsorbs an oil, such as an essential oil and allows the passing vapor to dissolve or take up small quantities of the oil for dispersion into the surrounding atmosphere. In some embodiments the oil-bearing material dissolves as the vapor passes, while in other embodiments only the oil enters the gas phase, leaving the solid material behind on the screen.

In some embodiments the apparatus is battery powered. In some embodiments the apparatus is plugged into a power source 50.

In closing, it is to be understood that the embodiments of the disclosure disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

What is claimed is:

1. A vapor generator comprising:
   a container with an opening;
   a receptacle housed inside the container;
   a fluid vaporizer housed inside the container;
   a vented lid configured to selectively cover the opening of the container wherein the lid comprises a plurality of air foils configured to direct and stall vapor leaving the receptacle; and
   a depression formed in the vented lid configured to received a substrate.

2. The vapor generator of claim 1 further comprising a liquid in the receptacle.

3. The vapor generator of claim 1 wherein the receptacle is removable.

4. The vapor generator of claim 1 wherein vaporizer is a heating element.

5. The vapor generator of claim 4 wherein heating element extends into the center of the receptacle.

6. The vapor generator of claim 4 wherein the heating element heats the receptacle.

7. The vapor generator of claim 1 wherein the vaporizer is a ultrasonic humidifier.

8. The vapor generator of claim 1 wherein the substrate is configured to be placed in the vapor stream.

9. The vapor generator of claim 8 wherein the substrate is a porous rock.

10. The vapor generator of claim 8 wherein the substrate is absorbent polymer beads.

11. A vapor generator comprising:
    a container with an opening;
    a receptacle housed inside the container;
    a fluid heater housed inside the container and form a vapor configured to escape the container;
    a lid comprising a screen and configured to selectively cover the opening of the container wherein the lid comprises a plurality of air foils configured to direct and concentrate vapor leaving the receptacle;
    a depression formed in the lid; and
    a substrate configured to hold an essential oil on the screen wherein vapor passes through the screen mixes with the essential oil and diffuses it into the ambient air.

12. The vapor generator of claim 11 wherein a plurality of vents are configured to direct the vapor at the substrate.

13. The vapor generator of claim 11 wherein the foils extend radially from the center and turns in a first direction, turns in a second direction and turn to continue in the first direction.

14. The vapor generator of claim 1 wherein the plurality of air foils form an undulating mesh configured to direct the vapor to engage the substrate comprising an essential oil.

15. The vapor generator of claim 11 wherein the substrate is selectively removable.

16. A vapor generator comprising:
    a container with an top opening;
    a fluid receptacle inside the container;
    a fluid vaporizer inside the container;
    a screen covering the opening wherein the screen comprises a plurality of air foils; and
    a depression.

17. The vapor generator of claim 16 wherein a portion of the air foils are proximally oriented and a portion of the air foils are distally oriented.

18. The vapor generator of claim 16 wherein a portion of the screen is recessed below the top edge of the container.

19. The vapor generator of claim 16 wherein the air foils are concentrically arranged.

* * * * *